United States Patent [19]

Curci et al.

[11] Patent Number: 5,457,172
[45] Date of Patent: Oct. 10, 1995

[54] (METH)ACRYLIC COMPOUNDS, PROCESS FOR THEIR PREPARATION AND THEIR APPLICATION TO THE SYNTHESIS OF NEW POLYMERS

[75] Inventors: Mich'ele Curci, Metz; Jean-Luc Mieloszynski, Montigny Les Metz; Daniel Paquer, Vandoeuvre, all of France

[73] Assignee: Elf Atochem S.A., Paris La Defense, France

[21] Appl. No.: 18,594

[22] Filed: Feb. 17, 1993

[30] Foreign Application Priority Data

Feb. 17, 1992 [FR] France ............... 92 01748

[51] Int. Cl.⁶ .................. C07C 327/20; C07C 69/34
[52] U.S. Cl. .................. 526/240; 526/286; 526/321; 526/318; 560/152; 560/190
[58] Field of Search .................. 560/152, 205, 560/190

[56] References Cited

U.S. PATENT DOCUMENTS

| | | | |
|---|---|---|---|
| 3,375,263 | 3/1968 | Trebilcock | 554/71 |
| 3,687,978 | 8/1972 | Federsen | 260/340.3 |
| 3,736,341 | 5/1973 | Diamond et al. | 260/405 |
| 3,888,912 | 6/1975 | Burguette | 260/486 R |

FOREIGN PATENT DOCUMENTS

| | | |
|---|---|---|
| 0020000 | 12/1980 | European Pat. Off. |
| 0367577 | 5/1990 | European Pat. Off. |
| 0463947 | 1/1992 | European Pat. Off. |
| 2035789 | 1/1971 | France . |
| 2285122 | 4/1976 | France . |
| 2398079 | 2/1979 | France . |
| 2071386 | 9/1991 | France . |
| 58-203171 | 11/1983 | Japan . |
| 2053203 | 2/1981 | United Kingdom . |

OTHER PUBLICATIONS

Kuzovleva, (v.sb., Organ Soedineniya Sery. (1976), 1 From: Ref. Zh. Khim., (1976) (Abstact only) w/CAS Search Report showing structures.

Krylova, et al. Zh. Prikl. Khim. (Leningrad) (1984), 57(12), 2719–22 (Abstract only).

*Primary Examiner*—José G. Dees
*Assistant Examiner*—Joseph M. Conrad
*Attorney, Agent, or Firm*—Millen, White, Zelano, & Branigan

[57] ABSTRACT

These compounds are denoted by the following formula (I):

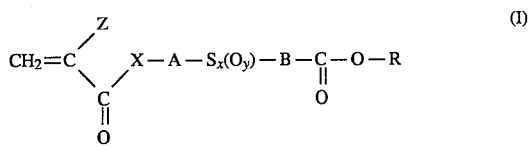

in which:
Z denotes H or a linear or branched alkyl radical,
X denotes O or S,
each of A and B independently denotes an alkylene radical, it being possible for this radical to be substituted,
R denotes H or an alkali metal, or else a linear or branched alkyl radical,
x has the value of 0 or 1, and
y has the value of 0, 1 or 2,
the radical A not existing if x and y are both equal to 0, X being incapable of denoting O when R=alkyl and when R=H with x=y=0, and B being incapable of denoting optionally substituted methylene when X=S, x=y=0 and R=alkyl.

According to the invention, different simple and efficient processes are proposed for preparing these new compounds, which can be applied to the preparation of new polymers and copolymers.

46 Claims, No Drawings

(METH)ACRYLIC COMPOUNDS, PROCESS FOR THEIR PREPARATION AND THEIR APPLICATION TO THE SYNTHESIS OF NEW POLYMERS

The present invention relates to a new class of (meth)acrylic compounds, to processes making it possible to obtain these compounds, and to the application of the latter to the synthesis of new polymers.

The invention is aimed at widening the available range of (meth)acrylic compounds, in particular sulphur-containing (meth)acrylic compounds, furthermore proposing simple and efficient processes for preparing these new compounds, applicable to the preparation of new polymers and copolymers.

The subject of the present invention is therefore (meth)acrylic compounds denoted by the following formula (I):

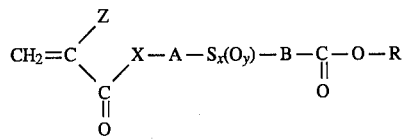

in which:

Z denotes H or a linear or branched alkyl radical,

X denotes O or S, each of A and B independently denotes an alkylene radical, it being possible for this radical to be substituted, R denotes H or an alkali metal, or else a linear or branched alkyl radical, x has the value of 0 or 1, and y has the value of 0, 1 or 2, the radical A not existing if x and y are both equal to 0, x being incapable of denoting O when R=alkyl and when R=H with x=y=0, and B being incapable of denoting optionally substituted methylene when X=S, x=y=0 and R=alkyl.

Methyl, ethyl, propyl, tert-butyl and n-butyl radicals may be mentioned as alkyl radicals forming part of the definition of Z or R.

The alkali metal forming part of the definition of R is chosen especially from sodium or potassium.

Preferred (meth)acrylic compounds are those in the case of which, in the formula (I), Z denotes H or a methyl radical, each of A and B independently denotes a residue —$(CH_2)_n$—, n denoting an integer from 1 to 20, R denotes H, an alkali metal or an alkyl radical, and X, x and y are as defined above.

The compounds denoted by the following formulae (Ia), (Ib) and (Ic):

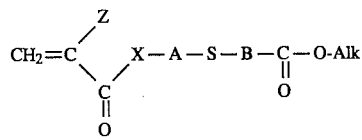

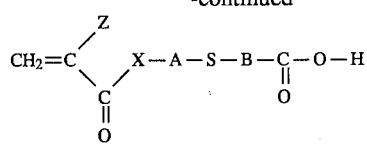

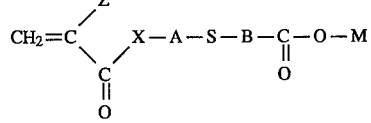

in which:

Z denotes H or a linear or branched alkyl radical, x denotes O or S, each of A and B independently denotes an optionally substituted alkylene radical, M denotes an alkali metal, and Alk an alkyl radical, can be prepared by a process according to which a compound denoted by the following formula (II):

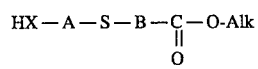

in which: X, A, B and Alk are as defined above, is reacted with a compound denoted by the following formula (III):

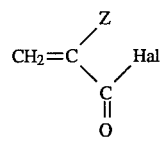

in which:

Z is as defined above, and

Hal denotes a halogen, in particular chlorine, bromine or iodine, and this produces a compound of the formula (Ia) which can be treated with H$^+$ ions to obtain an acid of formula (Ib) which can be converted into salt to obtain a salt of formula (Ic).

The tert-butyl radical as Alk in the compound (II) is preferred when it is desired to obtain the acid form (Ib), because the tert-butyl radical is that most easily removable.

The reaction of the compounds (II) and (III) is generally conducted with a slight molar excess of the compound (III) in relation to the compound (II), for example with a molar ratio compound (III)/compound (II) of 1.1/1, and in a solvent such as chloroform, carbon tetrachloride, methylene chloride or. an aromatic solvent such as toluene. The reaction is advantageously conducted at a temperature of 0° C. or in the neighbourhood of 0° C. during the addition of the compound (III), with subsequent return to room temperature, and for a period of the order of a few hours, for example approximately 24 hours.

The reaction of the compound of formula (II) and of the compound of formula (III) is furthermore generally performed in the presence of at least one compound capable of inhibiting the polymerisation of the compound of formula (III), employed, for example, in a proportion of approximately from 0.004% to 0.1% by weight based on the weight of the compound of formula (III). As examples of polymerisation inhibitors which can be employed there may be mentioned especially phenothiazine, hydroquinone monomethyl ether, N,N'-diethylhydroxylamine, nitrobenzene, di-tert-butylcatechol, hydroquinone, p-anilinophenol, di(2-ethylhexyl) octylphenyl phosphite, methylene blue and their mixtures in all proportions.

To obtain the acid (Ib), the compound (Ia) is treated with $H^+$ ions introduced using organic acids such as formic acid, or using inorganic acids.

The present invention also relates, by way of intermediates for the synthesis of the compounds of formula (Ia) as defined above, the compounds denoted by the formula (II):

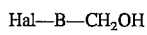  (II)

in which A, B and Alk are as defined above.

One of the following three processes can be employed for preparing these compounds of formula (II):

In accordance with the first process, a compound of the following formula (IV):

Hal—B—CH₂OH  (IV)

in which Hal denotes a halogen, in particular chlorine, bromine or iodine, and especially chlorine, and B is as defined above, is reacted with nitric acid, the compound of formula (V) thus obtained:

  (V)

is reacted with a compound of the following formula (VI):

Alk—OH  (VI)

in which Alk is as defined above, the compound of formula (VII) thus obtained:

  (VII)

is reacted with a compound of the following formula (VIII):

HS—A—XH  (VIII)

in which A and X are as defined above.

In accordance with the second process, a compound of the following formula (IX):

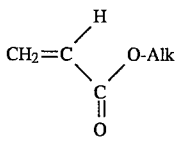  (IX)

in which Alk is as defined above, is reacted with a compound of the formula (VIII) as defined above, and this produces the compound of formula (IIa):

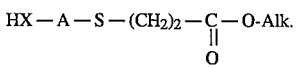  (IIa)

In accordance with the third process, a compound of the following formula (X):

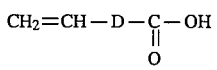  (X)

in which D has the same meanings as A or B above, is reacted with a compound of the formula (VI) as defined above, and the compound of the formula (XI) thus obtained:

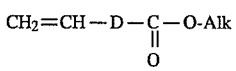  (XI)

is reacted with the compound of the formula (VIII) as defined above, and this produces a compound of formula (IIb):

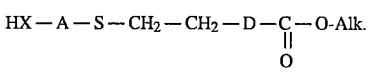  (IIb)

The compounds denoted by the following formulae (Id), (Ie) and (If):

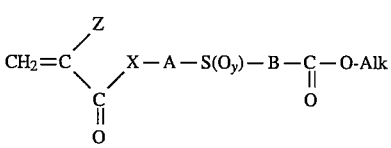  (Id)

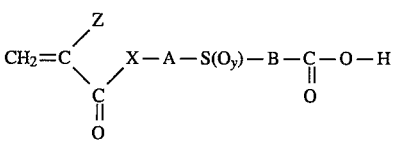  (Ie)

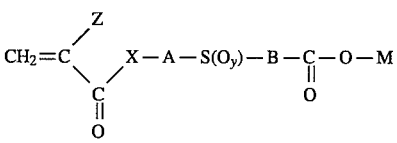  (If)

in which:

Z, X, A, B, Alk and M are as defined above, and y has the value of 1 or 2, are prepared by the process consisting in reacting a compound of formula (Ia) as defined above with an oxidising agent, the molar ratio oxidising agent/compound (Ia) being at least equal to 1 and lower than 2 in order to obtain a sulphoxide (y=1), and at least equal to 2 in order to obtain a sulphone (y=2), and this produces a compound of formula (Id), which can be treated with $H^+$ ions to obtain an acid of formula (Ie), which can be converted into salt to obtain a salt of formula (If).

The oxidising agent may be aqueous hydrogen peroxide, preferably at a concentration of approximately between 5% and 50%, an organic peracid such as peracetic acid, performic acid, oxygen, air, dimethyl sulphoxide, sodium periodate or meta-chloroperbenzoic acid.

The compounds denoted by the following formulae (Ig), (Ih) and (Ii):

$$CH_2=C\begin{matrix}Z\\ \diagdown\\ C-X-B-C-O\text{-Alk}\\ \parallel\quad\quad\parallel\\ O\quad\quad O\end{matrix} \qquad (Ig)$$

$$CH_2=C\begin{matrix}Z\\ \diagdown\\ C-X-B-C-O-H\\ \parallel\quad\quad\parallel\\ O\quad\quad O\end{matrix} \qquad (Ih)$$

$$CH_2=C\begin{matrix}Z\\ \diagdown\\ C-X-B-C-O-M\\ \parallel\quad\quad\parallel\\ O\quad\quad O\end{matrix} \qquad (Ii)$$

in which Z, B, X, Alk and M are as defined above, can be prepared by the process consisting in reacting a compound of formula (VII) as defined above with a compound of following formula (XII):

$$CH_2=C\begin{matrix}Z\\ \diagdown\\ \quad\quad X-M'\\ C\diagup\\ \parallel\\ O\end{matrix} \qquad (XII)$$

in which:

Z is as defined above,

X denotes O or S, and

M' denotes an alkali metal, for example lithium, sodium or potassium, and this produces a compound of formula (Ig), which can be treated with H$^+$ ions to obtain the acid of formula (Ih), which can be converted into salt to obtain the salt of formula (Ii).

The reaction of the (meth)acrylate of formula (XII) and of the compound of formula (VII) is performed at a temperature which depends on the boiling point of the compound of formula (VII), in a solvent medium such as acetonitrile, and in the presence of at least one phase transfer agent employed, for example, in a proportion of approximately from 5 to 30 mol % relative to the (meth)acrylate of formula (XII). Examples which may be mentioned of phase transfer agents which can be employed in accordance with this process are especially quaternary ammonium salts, quaternary phosphonium salts, quaternary arsenium salts, polyethylene glycol ethers, macroheterocyclic complexants of the class of aprotic cryptants such as those described in FR-A-2,398,079, and nonnitrogenous macrocyclic complexants such as those described in U.S. Pat. No. 3,687,978.

In the process according to the invention the (meth)acrylate of formula (XII) and the halogen compound are generally employed in proportions such that the ratio (meth)acrylate (XII)/compound (VII) is at least 1 and preferably approximately between 1.and 1.6. The reaction time is generally approximately between 30 minutes and 20 hours.

The present invention finally relates to the application of the new acrylic compounds described above to the constitution of new polymers and copolymers. More precisely, the present invention relates to polymers and copolymers comprising at least one unit derived from at least one (meth)acrylic compound of formula (I). Such (co)polymers may additionally contain at least one unit derived from at least one monomer which is copolymerisable with the said (meth)acrylic compound.

The following examples illustrate the present invention without, however, limiting its scope. The reference examples relate to the preparation of the starting compounds for the synthesis of compounds of the invention. In the examples, Me denotes methyl, Et ethyl, t-Bu t-butyl, HQME hydroquinone monomethyl ether and KMA potassium methacrylate. For the sake of simplification, the numbering of the examples is not continuous, a higher series of ten being started each time the preparation of a new series of compounds is described. The percentages shown are by weight, unless shown otherwise.

Reference examples 1 to 10

Synthesis of compounds of formula (II) in which: A=—(CH$_2$)$_2$—, B=—(CH$_2$)$_2$— with r as defined in Table 1, and Alk=t-Bu.

General operating method A $$Cl-(CH_2)_r-COO-t-Bu+HS-(CH_2)_2-OH \rightarrow HO-(CH_2)_2-S-(CH_2)_r-COO-t-Bu$$

1 mole of KOH is placed in 95° EtOH in a reactor fitted with a condenser, a thermometer and a magnetic stirring system. After dissolving at 50° C., 1 mole of mercaptoethanol is added and is left stirred for 30 minutes. After cooling to room temperature the chlorine derivative is added dropwise. The mixture is then refluxed for 4 hours. After cooling, the mixture is filtered and the filtrate is neutralised with 1N HCl. The product is extracted with CH$_2$Cl$_2$ and the ethanol is removed by repeated washing with water. The organic phase is dried and evaporated. The product is employed in the next stage without further purification.

General operating method B $$CH_2=CH-(CH_2)_{r-2}-COO-t-Bu+HS-(CH_2)_2-OH \rightarrow HO-(CH_2)_2-S-(CH_2)_r-COO-t-Bu$$

0.12 mole of mercaptoethanol and 0.1 mole of ethylene derivative are placed in 30 ml of cyclohexane in a reactor fitted with a condenser, a thermometer and a magnetic stirring system. The mixture is heated at 60° C. for at least 3 hours and, if appropriate, in the presence of a radical initiator such as azobisisobutyronitrile (accelerating the reaction rate). The organic phase is washed with a slightly basic solution (1N NaOH) and with water and is then dried and evaporated.

The results are reported in Table 1.

TABLE 1

| Reference compound | Operating method | r | Yield (%) |
|---|---|---|---|
| 1 | A | 1 | 90 |
| 2 | B | 2 | 95 |
| 3 | A | 3 | 97 |
| 4 | A | 4 | 97 |
| 5 | A | 5 | 90 |
| 6 | B | 10 | 57 |

Examples 11 to 21

Synthesis of compounds of formula (Ia) in which: X=O, A=—(CH$_2$)$_2$—, B=—(CH$_2$)$_b$— with b as defined in Table 2, and Alk=t-Bu.

General operating method C $$HO-(CH_2)_2-S-(CH_2)_b-COO\text{-}t\text{-}Bu +$$

-continued

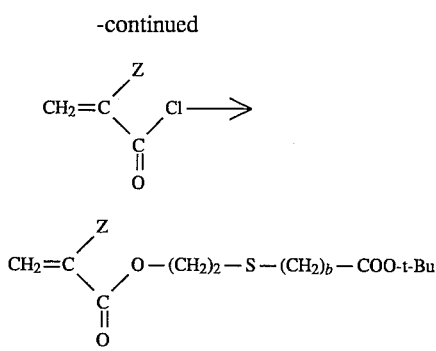

$$CH_2=C\begin{smallmatrix}Z\\ \\C\\\|\\O\end{smallmatrix}O-(CH_2)_2-S-(CH_2)_b-COO\text{-}t\text{-}Bu$$

0.1 mole of alcohol, 0.1 mole of triethylamine and 800 ppm of HQME are placed in a reactor fitted with a condenser, a thermometer and a magnetic stirring system. The mixture is cooled to 0° C. in an ice bath. 0.11 mole of (meth)acryloyl chloride is added as a solution in 20 ml of anhydrous $CHCl_3$, while the temperature is kept at 0° C. Stirring is continued at room temperature for 24 hours. 100 ml of $H_2SO_4$ (6N) are added and the mixture is extracted. The organic phase is washed successively with a 10% $KHCO_3$ solution and a solution saturated with NaCl. After drying, the solvent is evaporated off. The different esters obtained are purified by distillation or by chromatography on silica gel.

The results are reported in Table 2.

TABLE 2

| Compound of Example | Z | b | Chemical name | Alcohol prepared according to operating method | State | Yld (%) | B.p. (mbar) | Analysis |
|---|---|---|---|---|---|---|---|---|
| 11 | H | 1 | 2-[(1,1-Dimethylethoxycarbonyl)methylthio]ethyl 2-propenoate | A | Colourless liquid | 55 (distilled) | 110° C. (0.9) | $C_{11}H_{18}O_4S$ |
| 12 | Me | 1 | 2-[(1,1-Dimethylethoxycarbonyl)methylthio]ethyl 2-methyl-2-propenoate | A | Colourless liquid | 55 | | $C_{12}H_{20}O_4S$ |
| 13 | H | 2 | 2-[2-(1,1-Dimethylethoxycarbonyl)ethylthio]ethyl 2-propenoate | B | Colourless liquid | 88 (distilled) | 120° C. (0.5) | $C_{12}H_{20}O_4S$ |
| 14 | Me | 2 | 2-[2-(1,1-Dimethylethoxycarbonyl)ethylthio]ethyl 2-methyl-2-propenoate | B | Colourless liquid | 88 (distilled) | 140° C. (1.0) | $C_{13}H_{22}O_4S$ |
| 15 | H | 3 | 2-[3-(1,1-Dimethylethoxycarbonyl)propylthio]ethyl 2-propenoate | A | Colourless liquid | 60 | | $C_{13}H_{22}O_4S$ |
| 16 | Me | 3 | 2-[3-(1,1-Dimethylethoxycarbonyl)propylthio]ethyl 2-methyl-2-propenoate | A | Colourless liquid | 71 | | $C_{14}H_{24}O_4S$ |
| 17 | H | 4 | 2-[4-(1,1-Dimethylethoxycarbonyl)butylthio]ethyl 2-propenoate | A | Colourless liquid | 60 | | $C_{14}H_{24}O_4S$ |
| 18 | Me | 4 | 2-[4-(1,1-Dimethylethoxycarbonyl)butylthio]ethyl 2-methyl-2-propenoate | A | Colourless liquid | 58 | | $C_{15}H_{26}O_4S$ |
| 19 | H | 5 | 2-[5-(1,1-Dimethylethoxycarbonyl)pentylthio]ethyl 2-propenoate | A | Colourless liquid | 72 | | $C_{15}H_{26}O_4S$ |
| 20 | Me | 5 | 2-[5-(1,1-Dimethylethoxycarbonyl)pentylthio]ethyl 2-methyl-2-propenoate | A | Colourless liquid | 55 | | $C_{16}H_{28}O_4S$ |
| 21 | Me | 10 | 2-[10-(1,1-Dimethylethoxycarbonyl)decylthio]ethyl 2-methyl-2-propenoate | B | Colourless oil | 56 | | $C_{21}H_{36}O_4S$ |

| | $^1$H NMR (Solvent $CDCl_3$, Reference TMS) | | | | | | |
|---|---|---|---|---|---|---|---|
| Compound of Example | H trans to COO | H cis to COO | H gem to COO | $CH_2$—O | $CH_2$—S $CH_2$—CO | $CH_2$ | $CH_3$ |
| 11 | 5.8 m | 6.3 m | 6.1 m | 4.3 t | 2.9 t 3.1 s | | 1.5 s |
| 12 | 5.5 m | 6.1 m | /// | 4.55 t | 2.8 t 3.1 s | | 1.95 m 1.50 s |
| 13 | 5.8 m | 6.3 m | 6.1 m | 4.3 t | 2.4/2.9 m | | 1.45 s |
| 14 | 5.5 m | 6.1 m | /// | 4.3 t | 2.7 t 2.6 t | | 1.95 m 1.50 s |
| 15 | 5.8 m | 6.3 m | 6.1 m | 4.2 m | 2.2/2.8 m | 1.6 m | 1.4 s |
| 16 | 5.5 m | 6.1 m | /// | 4.3 m | 2.2/2.8 m | 1.6 m | 1.95 m 1.40 s |
| 17 | 5.8 m | 6.3 m | 6.1 m | 4.2 m | 2.2/2.8 m | 1.6 m | 1.4 s |
| 18 | 5.5 m | 6.1 m | /// | 4.25 t | 2.1/2.8 m | 1.6 m | 1.95 m 1.40 s |
| 19 | 5.8 m | 6.3 m | 6.1 m | 4.2 m | 2.0/2.8 m | 1.5 m | 1.4 s |
| 20 | 5.5 m | 6.1 m | /// | 4.15 m | 2.1/2.8 m | 1.5 m | 1.95 m 1.40 s |
| 21 | 5.5 m | 6.1 m | /// | 4.2 m | 2.1/2.8 m | 1.5 m | 1.95 m |

TABLE 2-continued 1.35 m $^{13}$C NMR (δ in ppm from the TMS; solvent CDCl$_3$); for C=O, the
first number shown is that of the —COO(CH$_2$)$_2$S(CH$_2$)$_b$COO-t-Bu group

| Compound of Example | CO | CH$_2$=C1 | CH= | O—CH$_2$ | CH$_2$—S | CH$_2$ | C and CH$_3$ | CH$_3$ Metha |
|---|---|---|---|---|---|---|---|---|
| 11 | 169.3<br>166.0 | 131.0 | 128.2 | 63.1 | 34.9<br>30.8 |  | 81.7<br>27.9 |  |
| 12 | 170.7<br>166.9 | 125.7 | 136.0 | 63.4 | 33.3<br>31.0 |  | 80.2<br>28.0 | 18.0 |
| 13 | 170.9<br>165.7 | 130.9 | 128.1 | 63.6 | 30.5<br>27.4 | 36.0 | 80.0<br>28.0 |  |
| 14 | 170.8<br>166.9 | 125.6 | 136.1 | 63.8 | 30.5<br>27.4 | 36.0 | 80.6<br>28.0 | 18.1 |
| 15 | 171.2<br>165.7 | 130.9 | 128.1 | 63.6 | 31.6<br>30.4 | 32.6<br>24.4 |  |  |
| 16 | 172.2<br>167.0 | 125.6 | 136.1 | 63.7 | 31.6<br>31.0 | 34.2<br>24.9 | 80.2<br>28.0 | 18.1 |
| 17 | 172.5<br>165.7 | 130.8 | 128.2 | 63.6 | 31.9<br>30.4 | 34.9<br>29.0<br>24.1 | 80.0<br>28.0 |  |
| 18 | 172.5<br>167.0 | 125.5 | 136.1 | 63.7 | 31.9<br>30.4 | 34.9<br>29.0<br>24.1 | 80.0<br>28.0 | 18.1 |
| 19 | 172.7<br>165.7 | 130.8 | 128.2 | 63.6 | 32.1<br>30.4 | 35.3<br>29.2<br>29.2<br>24.5 | 79.8<br>28.0 |  |
| 20 | 172.8<br>167.0 | 125.5 | 136.1 | 63.8 | 32.1<br>30.4 | 35.3<br>29.3<br>29.3<br>24.6 | 79.8<br>28.0 | 18.1 |
| 21 | 172.8<br>167.0 | 125.5 | 136.1 | 63.7 | Numerous signals |  | 79.8<br>28.0 | 18.1 |

Examples 31 to 41

Synthesis of compounds of formula (Ib) in which X=O, A=—(CH$_2$)$_2$—, B=—(CH$_2$)$_c$— with c as defined in Table 3.

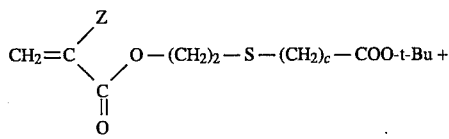

H$^+$ (for example HCOOH) ⟶

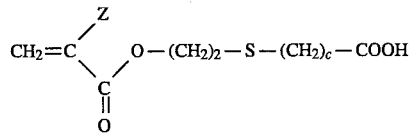

General operating method D

Formic acid (40 ml) and the tert-butyl ester (0.08 mole) are placed in a reactor fitted with a magnetic stirring system. They are left stirred at room temperature for 20 hours. The excess acid is evaporated off in vacuum. The residual oil is dissolved with stirring in a 10% NaHCO$_3$ solution (up to pH>9). The aqueous phase is washed with ethyl acetate and then acidified with concentrated HCl. The product is extracted with ethyl acetate. The organic phase is washed with water, dried and then evaporated.

The results are reported in Table 3:

TABLE 3

| Compound of Example | Z | C | Chemical name | State | Yield (%) | Analysis |
|---|---|---|---|---|---|---|
| 31 | H | 1 | 2-[(Carboxymethyl)thio]ethyl 2-propenoate | Colourless liquid | 80 | C$_7$H$_{10}$O$_4$S |
| 32 | Me | 1 | 2-[(Carboxymethyl)thio]ethyl 2-methyl-2-propenoate | Colourless liquid | 70 | C$_{18}$H$_{12}$O$_4$S |
| 33 | H | 2 | 2-[(2-Carboxyethyl)thio]ethyl 2-propenoate | Colourless liquid | 70 | C$_8$H$_{12}$O$_4$S |

TABLE 3-continued

| | | | | | | | |
|---|---|---|---|---|---|---|---|
| 34 | Me | 2 | 2-[(2-Carboxyethyl)thio]ethyl 2-methyl-2-propenoate | Colourless liquid | 70 | $C_9H_{14}O_4S$ |
| 35 | H | 3 | 2-[(3-Carboxypropyl)thio]ethyl 2-propenoate | Colourless liquid | 70 | $C_9H_{14}O_4S$ |
| 36 | Me | 3 | 2-[(3-Carboxypropyl)thio]ethyl 2-methyl-2-propenoate | Colourless liquid | 86 | $C_{10}H_{16}O_4S$ |
| 37 | H | 4 | 2-[(4-Carboxybutyl)thio]ethyl 2-propenoate | Colourless liquid | 83 | $C_{10}H_{16}O_4S$ |
| 38 | Me | 4 | 2-[(4-Carboxybutylthio)]ethyl 2-methyl-2-propenoate | Colourless liquid | 85 | $C_{11}H_{18}O_4S$ |
| 39 | H | 5 | 2-[(5-Carboxypentyl)thio]ethyl 2-propenoate | Colourless liquid | 74 | $C_{11}H_{18}O_4S$ |
| 40 | Me | 5 | 2-[(5-Carboxypentyl)thio]ethyl 2-methyl-2-propenoate | Colourless liquid | 75 | $C_{12}H_{20}O_4S$ |
| 41 | Me | 10 | 2-[(5-Carboxypentyl)thio]ethyl 2-propenoate | Colourless liquid | 50 | $C_{17}H_{30}O_4S$ |

$^1$H NMR (Solvent CDCl$_3$, Reference TMS)

| Compound of Example | H trans to COO | H cis to COO | H gem to COO | CH$_2$—O | CH$_2$—S CH$_2$—CO | CH$_2$ | OH (*) | CH$_3$ |
|---|---|---|---|---|---|---|---|---|
| 31 | 5.8 m | 6.3 m | 6.1 m | 4.3 t | 2.9 t<br>3.3 s | | 11.0 | |
| 32 | 5.5 m | 6.1 m | /// | 4.4 t | 2.95 t<br>3.3 s | | 9.6 | 2.0 m |
| 33 | 5.8 m | 6.3 m | 6.1 m | 4.3 t | 2.8 m | | 10.9 | |
| 34 | 5.55 m | 6.1 m | /// | 4.3 t | 2.5/3.0 m | | 10.6 | 2.0 m |
| 35 | 5.8 m | 6.3 m | 6.1 m | 4.3 t | 2.2/2.9 m | 1.6 m | 10.5 | |
| 36 | 5.55 m | 6.1 m | /// | 4.25 m | 2.5/3.0 m | 1.6 m | 10.0 | 2.0 m |
| 37 | 5.8 m | 6.3 m | 6.1 m | 4.3 t | 2.3/2.8 m | 1.7 m | 11.2 | |
| 38 | 5.55 m | 6.1 m | /// | 4.25 m | 2.5/3.0 m | 1.6 m | 10.0 | 2.0 m |
| 39 | 5.8 m | 6.3 m | 6.1 m | 4.3 m | 2.2/2.9 m | 1.7 m | 10.7 | |
| 40 | 5.55 m | 6.1 m | /// | 4.25 m | 2.5/3.0 m | 1.6 m | 9.8 | 2.0 m |
| 41 | 5.55 m | 6.1 m | /// | 4.2 m | 2.5/3.0 m | 1.4/2.0 m | 9.6 | 1.9 m |

$^{13}$C NMR (δ in ppm from the TMS; solvent CDCl$_3$); for C═O, the first number shown is that of the —COO(CH$_2$)$_2$S(CH$_2$)$_c$COO-t-Bu group

| Compound of Example | CO | CH$_2$═ Cl | CH═ | O—CH$_2$ | CH$_2$—S | CH$_2$ | C and CH$_3$ | CH$_3$ Metha |
|---|---|---|---|---|---|---|---|---|
| 31 | 175.7<br>166.0 | 131.3 | 127.9 | 63.0 | 33.3<br>31.0 | | | |
| 32 | 175.6<br>167.2 | 126.0 | 135.9 | 63.2 | 33.3<br>31.0 | 33.3 | | 18.1 |
| 33 | 177.3<br>165.9 | 131.1 | 128.0 | 63.5 | 30.5<br>26.8 | 34.5 | | |
| 34 | 177.4<br>167.2 | 125.8 | 136.0 | 63.7 | 30.6<br>26.8 | 34.6 | | 18.1 |
| 35 | 178.8<br>166.0 | 131.1 | 128.1 | 63.6 | 31.4<br>30.2 | 32.6<br>24.4 | | |
| 36 | 178.8<br>167.2 | 125.7 | 136.0 | 63.7 | 31.4<br>30.2 | 32.5<br>24.4 | | 18.1 |
| 37 | 179.2<br>165.8 | 130.9 | 128.1 | 63.6 | 31.8<br>30.3 | 33.3<br>28.8<br>23.6 | | |
| 38 | 179.2<br>167.2 | 125.7 | 136.1 | 63.8 | 31.9<br>30.4 | 33.4<br>28.9<br>23.7 | | 18.1 |
| 39 | 179.5<br>165.9 | 131.0 | 128.2 | 63.7 | 32.1<br>30.4 | 33.8<br>29.2<br>28.1<br>24.1 | | |
| 40 | 179.6<br>167.1 | 125.7 | 136.1 | 63.9 | 32.0<br>30.4 | 33.8<br>29.2<br>28.0<br>24.1 | | 18.1 |
| 41 | 179.6<br>167.1 | 125.7 | 136.1 | 63.9 | numerous signals | | | 18.1 |

*δ variable with dilution; this signal disappears on treatment with D$_2$O.

Examples 51 to 54

Synthesis of the compounds of formula (Id) or (Ie) in which: Z=Me, X=O, A=—(CH$_2$)$_2$—, Y=1 or 2, B=—(CH$_2$)$_2$—, Alk=t-Bu.

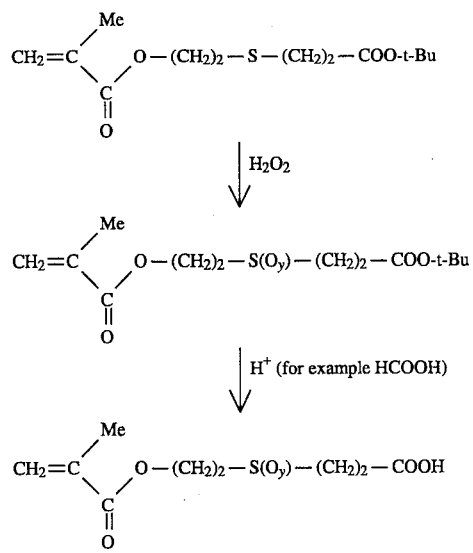

General operating method E

E1: Preparation of a sulphoxide (y=1)

0.1 mole of acrylic sulphide is placed in a reactor fitted with a condenser, a thermometer and a magnetic stirring system. 0.11 mole of 30% strength aqueous hydrogen peroxide is introduced dropwise into this reactor, kept at 0° C. When the addition is finished, the mixture is stirred at room temperature for 24 hours. The mixture obtained is extracted with chloroform. After drying of the organic phase the final compound is obtained by evaporation of the solvent.

E2: Preparation of a sulphone (y=2)

0.1 mole of acrylic sulphide is placed in a reactor fitted with a condenser, a thermometer and a magnetic stirring system. 0.22 mole of 30% strength aqueous hydrogen peroxide is introduced dropwise into this reactor, kept at 7° C. When the addition is finished, the mixture is stirred at room temperature for 24 hours and then heated at 45° C. for 72 hours. The mixture obtained is extracted with chloroform. After drying of the organic phase, the final compound is obtained by evaporation of the solvent.

The results obtained are reported in Table 4.

Examples 61 to 64 and 71 to 73

Synthesis of the compounds of formula (Ig) or (Ih) in which: Z=Me, B=—(CH$_2$)$_e$— with e as defined in Table 5, and Alk=t-Bu.

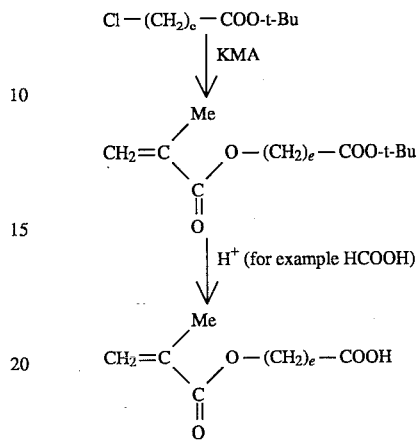

General operating method F

KMA (0.15 mole), t-butyl chloroester (0.1 mole), tricaprylylmethylammonium chloride (marketed by Fluka under the name Aliquat® 336) in a proportion of 5 to 10% by weight relative to KMA, 800 ppm of HQME and 150 ml of acetonitrile are placed in a reactor fitted with a condenser, a thermometer and a magnetic stirring system. The mixture is refluxed at 80° C. for 24 hours. After returning to room temperature, the mixture is filtered and the solvent is evaporated off. The product is purified by distillation in the presence of HQME as stabiliser.

The corresponding acids are then obtained by applying the operating method D.

The results obtained are reported in Table 5.

TABLE 4

| Compound of Example | Y | R | Chemical name | State | Yield (%) | Analysis |
|---|---|---|---|---|---|---|
| 51 | 1 | t-Bu | 2-[2-(1,1-Dimethylethoxycarbonyl)ethylsulphinyl]ethyl 2-methyl-2-propenoate | Colourless liquid | 86 | C$_{13}$H$_{22}$O$_5$S |
| 52 | 2 | t-Bu | 2-[2-(1,1-Dimethylethoxycarbonyl)ethylsulphonyl]ethyl 2-methyl-2-propenoate | Colourless liquid | 95 | C$_{13}$H$_{22}$O$_6$S |
| 53 | 1 | H | 2-[(2-Carboxyethyl)sulphinyl]ethyl 2-methyl-2-propenoate | Colourless liquid (soluble in water) | 94 | C$_9$H$_{14}$O$_5$S |
| 54 | 2 | H | 2-[(2-Carboxyethyl)sulphonyl]ethyl 2-methyl-2-propenoate | Colourless liquid | 81 | C$_9$H$_{14}$O$_6$S |

TABLE 5

| Compound of Example | e | R | Nomenclature | State | Yield (%) | B.p. (mbar) | Analysis |
|---|---|---|---|---|---|---|---|
| 61 | 1 | t-Bu | 1,1-Dimethylethoxycarbonylmethyl 2-methyl-2-propenoate | Colourless liquid | 84 | 60° C. (0.4) | $C_{10}H_{16}O_4$ |
| 62 | 3 | t-Bu | 2(1,1-Dimethylethoxycarbonyl)ethyl 2-methyl-2-propenoate | Colourless liquid | 84 | 95° C. (1.0) | $C_{12}H_{20}O_4$ |
| 63 | 4 | t-Bu | 4-(1,1-Dimethylethoxycarbonyl)butyl 2-methyl-2-propenoate | Colourless liquid | 55 | 106° C. (1.0) | $C_{13}H_{22}O_4$ |
| 64 | 5 | t-Bu | 5-(1,1-Dimethylethoxycarbonyl)pentyl 2-methyl-2-propenoate | Colourless liquid | 67 | 106° C. (0.5) | $C_{14}H_{24}O_4$ |
| 71 | 3 | H | 3-Carboxypropyl 2-methyl-2-propenoate | oil | 93 | | $C_8H_{12}O_4$ |
| 72 | 4 | H | 4-Carboxybutyl 2-methyl-2-propenoate | oil | 91 | | $C_9H_{14}O_4$ |
| 73 | 5 | H | 5-Carboxypentyl 2-methyl-2-propenoate | oil | 71 | | $C_{10}H_{16}O_4$ |

| Compound of Example | $^1$H NMR | | | | | | RMN $^{13}$C | | | | | |
|---|---|---|---|---|---|---|---|---|---|---|---|---|
| | Ha (trans) trans/COOR | Hb (cis) cis/COOR | $CH_2$—O | $CH_2$ | OH | $CH_3$ | CO | $CH_2$= | C= | O—$CH_2$ | $CH_2$ | $CH_3$ Metha |
| 71 | 5.5 m | 6.0 m | 4.1 m | 2.3 m 1.6 m | 10.5 m | 1.95 m | 178.5 167.3 | 125.5 | 136.1 | 63.5 | 30.5 23.7 | 18.1 |
| 72 | 5.5 m | 6.0 m | 4.1 m | 2.3 m 1.6 m | 11.5 | 1.95 m | 179.3 167.4 | 125.3 | 136.3 | 64.1 | 33.4 27.9 21.2 | 18.1 |
| 73 | 5.3 m | 6.0 m | 4.1 m | 2.3 m 1.6 m | 9.0 | 2.0 m | 179.5 167.5 | 125.2 | 136.4 | 64.4 | 33.8 28.2 25.4 24.2 | 18.1 |

*The operating methods F and then D were employed for compounds 71 to 73.

Operating method H
Preparation of the metal salts of the acids

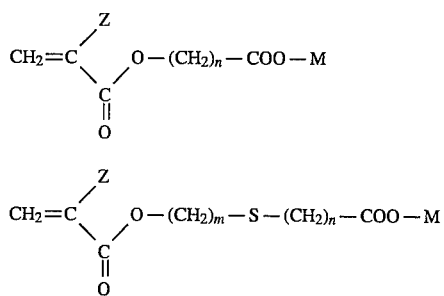

Starting with all the proposed acidic compounds (sulphur-containing or otherwise), the corresponding metal salts (Na, K, etc.) can be prepared by the following general process:

0.1 mole of a (meth)acrylic acid, sulphur-containing or otherwise, is introduced into a reactor, followed by 0.1 mole of a 10% strength alkaline solution. The water is evaporated off by azeotropic distillation with cyclohexane in the presence of HQME as stabiliser. The desired salt is thus isolated.

All of the polymers and copolymers mentioned in the preceding description of the invention can be used in the same manner as conventional (meth)acrylic compounds, e.g., they can be molded or cast into desired shapes or can be used as binders or vehicles in coating compositions.

The entire disclosure of all applications, patents, and publications, cited above and below, and of corresponding French Application 92-01748, filed Feb. 17, 1992, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. An acrylic compound of formula (I):

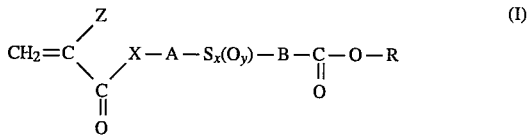

wherein:

Z is H or a linear or branched alkyl radical,

X is O or S, each of A and B independently is an unsubstituted or substituted alkylene radical, R is H, an alkali metal, or a linear or branched alkyl radical, x has the value of 0 or 1, and y has the value of 0, 1 or 2, but is 0 when x=0, with the following provisos:
(a) the radical A does not exist if x and y are both equal to 0;
(b) X is S when R=alkyl with x=y=0, or with x=1 and y=0, or with x=1 and y=2; or when R=H or alkali metal with x=y= 0;
(c) B is not substituted methylene when X=S, x=y=0 and R=alkyl;
(d) R is H, when X=S with Z=alkyl and x=y= 0;
(e) —A—$S_x(O)_y$—B— is other than methylene when X= S and when Z=H with R=H, or Z=H with R=alkyl, or Z=alkyl with R=alkyl; and
(f) B is not substituted ethylene when X=S, x= y=0, Z=H, and R=H.

2. An acrylic compound according to claim 1, wherein in formula (I),

Z is H or a methyl radical, each of A and B independently is a residue —$(CH_2)_n$—, n denoting an integer from 1 to 20, and R is H, an alkali metal or an alkyl radical.

3. A polymer containing at least one unit of at least one compound of the formula (I) as defined in claim 1.

4. An acrylic compound according to claim 1, wherein Z is H.

5. An acrylic compound according to claim 1, wherein X is O, except when R=alkyl with x= y=0, with x=1 and y=0, or with x=1 and y=2; or when R=H with x=y=0.

6. An acrylic compound according to claim 5, wherein R is isobutyl.

7. A polymer containing at least one unit of at least one compound of formula I as defined in claim 6.

8. An acrylic compound according to claim 1, wherein A is —$(CH_2-CH_2)$— and B represents —$(CH_2)$—.

9. An acrylic compound according to claim 8, wherein R is isobutyl.

10. An acrylic compound according to claim 1, wherein R is alkyl.

11. An acrylic compound according to claim 1, wherein R is isobutyl.

12. Acrylic compound according to claim 11, wherein x is 1 and y is 0.

13. A compound according to claim 1, wherein X is S.

14. A polymer containing at least one unit of at least one compound of formula I as defined in claim 13.

15. An acrylic compound according to claim 13 wherein R is isobutyl.

16. A polymer containing at least one unit of at least one compound of formula I as defined in claim 15.

17. An acrylic compound according to claim 1, wherein R= alkyl, X=S, x=y=0, and B is not substituted ethylene.

18. An acrylic compound according to claim 17, wherein Z is a linear or branched alkyl radical.

19. An acrylic compound of formula (I):

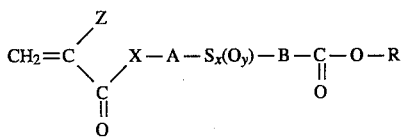

(I)

wherein:

Z is H or a linear or branched alkyl radical,

X is O or S, each of A and B independently is an unsubstituted or substituted alkylene radical, R is H, an alkali metal, or a linear or branched alkyl radical, x has the value of 1, and y has the value of 0, 1 or 2, with the proviso that X is S when R=alkyl with y=0, or with y=2.

20. An acrylic compound according to claim 19, wherein x is 1 and y=0.

21. A polymer containing at least one unit of at least one compound of claim 20.

22. An acrylic compound according to claim 20, wherein A is —$CH_2-CH_2$— and B is —$CH_2$—.

23. An acrylic compound according to claim 22, wherein R is isobutyl.

24. A polymer containing at least one unit of at least one compound of claim 23.

25. A polymer containing at least one unit of at least one compound of claim 22.

26. An acrylic compound according to claim 20, wherein R is isobutyl.

27. A polymer containing at least one unit of at least one compound of claim 26.

28. An acrylic compound according to claim 19, wherein A is —$CH_2-CH_2$— and B is —$CH_2$—.

29. An acrylic compound according to claim 28, wherein R is isobutyl.

30. A polymer containing at least one unit of at least one compound of claim 29.

31. A polymer containing at least one unit of at least one compound of claim 28.

32. An acrylic compound according to claim 19, wherein R is isobutyl.

33. A polymer containing at least one unit of at least one compound of claim 32.

34. A polymer containing at least one unit of at least one compound of claim 19.

35. An acrylic compound which is 2-[1,1-dimethylethoxycarbonyl)methylthio]ethyl 2-propenoate or 2-[(1,1-dimethylethoxycarbonyl)methylthio]ethyl 2-methyl-2-propenoate.

36. A polymer containing at least one unit of at least one compound of the formula (I) as defined in claim 35.

37. An acrylic compound which is 2-[(1,1-dimethylethoxycarbonyl)methylthio]ethyl-2-propenoate.

38. A polymer containing at least one unit of at least one compound of the formula (I) as defined in claim 37.

39. An acrylic compound being:

2-[(1,1-dimethylethoxycarbonyl)methylthio]ethyl 2-propenoate,

2-[(1,1-dimethylethoxycarbonyl)methylthio]ethyl 2-methyl-2-propenoate,

2-[(2-(1,1-dimethylethoxycarbonyl)ethylthio]ethyl 2-propenoate,

2-[2-(1,1-dimethylethoxycarbonyl)ethylthio]ethyl 2-methyl-2-propenoate,

2-[3-(1,1-dimethylethoxycarbonyl)propethylthio]ethyl 2-propenoate,

2-[3-(1,1-dimethylethoxycarbonyl)propethylthio]ethyl 2-methyl-2-propenoate,

2-[4-(1,1-dimethylethoxycarbonyl)butylthio]ethyl 2-proponoate,

2-[4-(1,1-dimethylethoxycarbonyl)butylthio]ethyl 2-methyl-2-propenoate,

2-[5-(1,1-dimethylethoxycarbonyl)pentylthio]ethyl 2-propenoate,

2-[5-(1,1-dimethylethoxycarbonyl)pentylthio]ethyl 2-methyl-2-propenoate, or

2-[10-(1,1-dimethylethoxycarbonyl)decylthio]ethyl 2-methyl-2-propenoate.

40. A polymer containing at least one unit of at least one compound of formula (I) as defined in claim 39.

41. An acrylic compound being:

2-[(carboxymethyl)thio]ethyl 2-propenoate,

2-[(carboxymethyl)thio]ethyl 2-methyl-2-propenoate,

2-[(carboxymethyl)thio]ethyl 2-propenoate,

2-[(carboxyethyl)thio]ethyl 2-methyl-2-propenoate,

2-[(carboxypropyl)thio]ethyl 2-propenoate,

2-[(carboxypropyl)thio]ethyl 2-methyl-2-propenoate,

2-[(4-(carboxypropyl)thio]ethyl 2-propenoate,

2-[(4-(carboxybutyl)thio]ethyl 2-methyl-2-propenoate,

2-[(5-(carboxympentyl)thio]ethyl 2-propenoate,

2-[(5-(carboxymethyl)thio]ethyl 2-methyl-2-propenoate, or

2-[(5-(carboxypentyl)thio]ethyl 2-propenoate.

42. A polymer containing at least one unit of at least one compound of formula (I) as defined in claim 41.

43. An acrylic compound being:

2-[2-(1,1-dimethylethoxycarbonyl)ethylsulphinyl]ethyl 2-methyl-2-propenoate,

2-[2-(1,1-dimethylethoxycarbonyl)ethylsulphonyl]ethyl 2-methyl-2-propenoate,

2-[(2-carboxyethyl)sulphinyl]ethyl 2-methyl-2-propenoate, or

44. A polymer containing at least one unit of at least one compound of formula (I) as defined in claim 43.

45. An acrylic compound of formula (I):

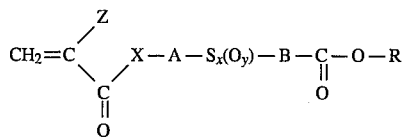

wherein:

Z is H or a linear or branched alkyl radical,

X is oxygen or sulfur, each of A and B independently is an unsubstituted or substituted alkylene radical, R is H, an alkali metal, or a linear or branched alkyl radical, x has the value of 0 or 1, and y has the value of 0, 1 or 2, but is 0 when x=0, with the following provisos:

(a) the radical A does not exist if x and y are both equal to 0;

(b) X is oxygen except when R=alkyl with x=y=0, or with x=1 and y=0, or with x=1 and y=2, or when R=H or alkali metal with x=y=0;

(c) B is not substituted methylene when X=S and x=y=0.

46. A polymer containing at least one unit of at least one compound of claim 45.

* * * * *